US006509026B1

(12) United States Patent
Ashkar et al.

(10) Patent No.: US 6,509,026 B1
(45) Date of Patent: Jan. 21, 2003

(54) OSTEOPONTIN COATED SURFACES AND METHODS OF USE

(75) Inventors: Samy Ashkar, Boston, MA (US); Jairo Salcedo, Boston, MA (US)

(73) Assignee: Children's Medical Center Corporation, Boston, MA (US)

( * ) Notice: Subject to any disclaimer, the term of this patent is extended or adjusted under 35 U.S.C. 154(b) by 0 days.

(21) Appl. No.: 09/134,253

(22) Filed: Aug. 14, 1998

Related U.S. Application Data

(63) Continuation-in-part of application No. 08/916,912, filed on Aug. 15, 1997, now abandoned.

(51) Int. Cl.[7] .................. A61K 38/16; A61K 38/18
(52) U.S. Cl. .............. 424/422; 424/423; 530/300; 530/324; 433/40; 433/172; 623/11.11
(58) Field of Search ............... 623/11.11; 433/40, 433/172; 424/422, 423; 530/300, 324

(56) References Cited

U.S. PATENT DOCUMENTS

| | | | |
|---|---|---|---|
| 5,372,503 A | * 12/1994 | Elia | 433/215 |
| 5,736,132 A | * 4/1998 | Juergensen et al. | 424/94.5 |
| 5,759,033 A | * 6/1998 | Elia | 433/173 |
| 5,824,651 A | * 10/1998 | Nanci et al. | 514/21 |
| 6,022,887 A | * 2/2000 | Gasper et al. | 514/451 |
| 6,165,487 A | * 12/2000 | Ashkar et al. | |

FOREIGN PATENT DOCUMENTS

| | | |
|---|---|---|
| WO | WO 93/07910 | 4/1993 |
| WO | WO94/26321 | 11/1994 |
| WO | WO 97/35000 | 9/1997 |
| WO | WO 98/07750 | 2/1998 |

OTHER PUBLICATIONS

Young et al., 1990, Genomics 7:491–502.*
Kiefer et al., 1989, Nucleic Acids Research 17:3306.*
Wells, 1990, Biochemistry 29:8509–8517.*
Ngo et al., 1994, The Protein Folding Problem and Tertiary Structure Prediction, Merz et al., eds., Birkhauser, Boston, pp. 492–495.*
Bork, 2000, Genome Research 10:398–400.*
Skolnick et al., 2000, Trends in Biotechnology 18:34–39.*
Doerks et al., 1998, Trends in Genetics 14:248–250.*
Smith et al., 1997, Nature Biotechnology 15:1222–1223.*
Brenner, 1999, Trends in Genetics 15:132–133.*
Bork et al., 1996, Trends in Genetics 12:425–427.*
Nanci, A. et al. (1994) "Tissue Response to Titanium Implants in the Rat Tibia: Ultrastructural, Immunocytochemical and Lectin–Cytochemical Characterization of the Bone–Titanium Interface", Cells and Materials, vol. 4, (1), 1–30.

McKee et al. (1994), "Osteopontin Antigenicity in Cementum: An Immunocytochemical and Developmental Study", *J Dent Res* 73 Abstract No. 2192.

McKee, M.D. et al., (1996), "Extracellular Matrix in Tooth Cementum and Mantle Dentin: Localization of Osteopontin and Other Nonconcollagenous Proteins, Plasma Proteins, and Glycoconjugates by Electron Microscopy", *The Anatomical Record*, vol. 245:293–312.

McKee, M.D. et al. (1996), "Osteopontin at Mineralized Tissue Interfaces in Bone, Teeth, and Osseointegrated Implants: Ultrastructural Distribution and Implications for Mineralized Tissue Formation, Turnover, and Repair", *Microscopy Research and Technique*, vol. 33:141–164.

McKee, M.D. et al. (1996), "Osteopontin Deposition in Remodeling Bone An Osteoblast Mediated Event", *Journal of Bone and Mineral Research*, vol. 11, (6), 873–875.

Butler, W.T. et al. (1996), "Osteopontin", *Principles of Bone Biology*, 167–181.

Khan, S.R. et al. (1996), "Osteopontin in Organic Matrix of Calcium Oxalate Crystals and Stones", *Journal of Urology* vol. 155, (5), Abstract No. 642A.

McKee, M.D. et al. (1996), "Osteopontin: An Interfacial Extracellular Matrix Protein in Mineralized Tissues", *Connective Tissue Research* vol. 35 (1–4), 197–205.

Nasu, K., et al., (1995) "Expression of Wild–type and mutated rabbit osteopontin in *Escherichia coli*, and their effects on adhesion and migration of P388D1 cells" Biochemical Journal, vol. 307(1), pp. 257–365.

Ullrich, O., et al. (1991) "Biosyntheses and Secretion of an Osteopontin–related 20–kDa Polypeptide in the Madin–Darby Canine Kidney Cell Line" Journal Of Biological Chemistry, vol. 266(6), pp. 3518–3525.

Dijk, V. S., et al. (1993) "Evidence That a Non–RGD Domain in Rat Osteopontin Is Involved in Cell Attachment" Journal Of Bone And Mineral Research, vol. 8(12), pp. 1499–1506.

Jian–Wu Xuan et al.(1995) "Site–Directed Mutagenesis of the Arginine–Glycine–Aspartic Acid Sequence in Osteopontin Destroys Cell Adhesion and Migration Functions" Journal of Cellular Biochemistry, vol. 57, pp. 680–690.

* cited by examiner

*Primary Examiner*—Elizabeth Kemmerer
(74) *Attorney, Agent, or Firm*—Holland & Knight LLP

(57) ABSTRACT

A novel osteopontin containing implant which increases the rate of osseointegration and the percentage of bone apposition is described. The implant of the invention includes a material suitable for use in vivo within a subject in combination with a releasable form of osteopontin forming an osteopontin containing implant.

12 Claims, 3 Drawing Sheets

OSTEOPONTIN COATED SURFACES AND METHODS OF USE

This application is a continuation-in-part application of U.S. Ser. No. 08/916,912 filed on Aug. 15, 1997 now abandoned, the contents of which are hereby incorporated by reference.

BACKGROUND OF THE INVENTION

The process that leads to successful osseointegration of an implant into the surrounding tissues is a complex one that involves cell migration, attachment, differentiation, proliferation, extracellular matrix synthesis and finally mineralization of that matrix. Implant materials are as biocompatible as their surface chemistry allows for a favorable interaction with the biological molecules relevant for that tissue.

For example, placement of endosseous dental implants has been limited to areas of favorable bone character, and fixtures must remain unloaded after placement for considerable periods of time. The primary challenges faced in the fabrication of new endosseous implants are to increase the rate of osseointegration and the percentage of bone apposition. Histological analysis of integrated titanium (Ti) implants into bone tissue revealed that many clinically successful implants are among 30–60% opposed directly by mineralized bone. The rest of the implant surface has been found to be apposed by fibrous tissue and unmineralized collagen fibers. It is desirable that the entire circumference of the osseointegrated implant be directly apposed by mineralized bone tissue.

Extracellular matrix proteins, especially certain adhesion molecules, play a role in bone repair and morphogenesis. These molecules can modulate gene expression through cell surface-extracellular matrix interactions. The interaction between the titanium oxide layer of dental implants and certain extracellular matrix proteins may be a prerequisite for reproducible direct apposition of bone to titanium implants.

Human osteoblast cell lines undergo a coordinated temporal expression of osteoblast phenotypic markers during their differentiation in vitro and produce a mineralized extracellular matrix. This bone developmental system is ideal for studying the interaction between titanium surfaces and bone cells in vitro.

SUMMARY OF THE INVENTION

The implants of the invention are improved implants which increase the rate of osseointegration and the percentage of bone apposition. Implant surfaces should have such properties which permit the phenomenology of the relevant cells. The achievement of reproducible biological integration of implants calls for a delineation of the molecular biological events relevant to the morphogenesis of the desired interfacial tissue. Material surfaces that can not bind the macromolecules supportive of osteoblast function, are not likely to make a good bone implant.

An enhanced rate of osseointegration and/or augmented percentage of bone apposition around implants or cell recruitment systems of the invention increases implant placement indications, expedites loading time, and opens new fields for research in implant materials.

Accordingly, the present invention provides a novel osteopontin containing implant. In an embodiment the coated implant increases the rate of osseointegration and the percentage of bone apposition. The implant of the invention includes a material suitable for use in vivo within a subject in combination with a releasable form of osteopontin forming an osteopontin containing implant.

In another aspect of the invention, the implant includes a material suitable for use in vivo within a subject in combination with at least two osteopontin polypeptides forming an osteopontin containing implant.

In another aspect of the invention, the implant includes a material suitable for use in vivo within a subject in combination with at least two osteopontin active polypeptides, wherein the active polypeptides are attached to the material such that upon implantation into the subject the osteopontin containing implant induces new bone formation.

In yet another aspect of the invention, the implant includes a material suitable for use in vivo within a subject in combination with a releasable form of osteopontin, wherein the osteopontin is attached to the material such that upon implantation into the subject the osteopontin containing implant induces new bone formation.

In still another aspect of the invention, the implant includes a material suitable for use in vivo within a subject in combination with an active osteopontin peptide forming an osteopontin containing implant.

In another aspect the invention features an osteopontin containing titanium implant. The implant includes a releasable form of phosphorylated osteopontin in combination with titanium suitable for use in vivo within a subject forming an osteopontin containing titanium implant.

In yet another aspect the invention features a method of coating an implant with an osteopontin or an active fragment thereof. The method includes non-covalently or electrostatically attaching osteopontin or an active fragment thereof to a surface of an implant, wherein the osteopontin or an active fragment thereof is attached to the surface of the implant such that it is releasable from the surface upon implantation into a subject.

In still another aspect the invention features a method of inducing new bone formation in a subject. The method includes implanting an osteopontin containing implant into a subject, wherein the osteopontin is released from the implant into the subject thereby inducing new bone formation in the subject.

In another aspect the invention features a method of inducing new bone formation in a subject at a site where bone formation is needed. The method includes implanting an osteopontin containing implant into a subject at a site where bone formation is needed, wherein the osteopontin is released from the implant into the site thereby inducing new bone formation at the site.

In another aspect the invention features an osteopontin containing cell recruitment system. The system includes a releasable osteopontin or a fragment thereof in a form which provides a gradient and an implant, forming a cell recruitment system in the proximity of the implant, wherein the implant is targeted for cell recruitment by a gradient of osteopontin which forms in the proximity of the implant.

In another aspect the invention feature a packaged releasable osteopontin or a fragment thereof for use in a cell recruitment system. The package includes a releasable osteopontin or a fragment thereof in a form which provides a gradient in the proximity of an implant which is targeted for cell recruitment by the gradient of osteopontin, packaged with instructions for use of said osteopontin or a fragment thereof with the implant targeted for cell recruitment.

In another aspect the invention features a coated osseointegrator capable of implantation. The osseointegrator includes a coated material which is enhanced for ooseointegration by at least about 100% when compared to an uncoated material based on the human osteoblast cell (HOS) attachment assay.

In another aspect the invention features a coated implant. The implant includes a coated material which increases the proliferation of osteoblasts by at least about 100% when compared to an uncoated material based on the human osteoblast cell (HOS) proliferation assay.

In still another aspect, the invention features a method for inducing new tissue formation in a subject at a site where tissue formation is needed. The method includes adding osteopontin into a subject at a site where tissue formation is needed, wherein the osteopontin induces new tissue formation about the site.

In yet another aspect, the invention features an osteopontin glue which includes osteopontin, a mucopolysaccharide and a multivalent metal, e.g., calcium, magnesium or manganese. Preferably, the osteopontin is at a concentration of about 100 µg/g of glue.

DETAILED DESCRIPTION OF THE DRAWINGS

FIG. 1 a graph depicting the effect of Ca++ ions on the binding of osteopontin to Titanium disks.

DETAILED DESCRIPTION OF THE INVENTION

Figure 1:
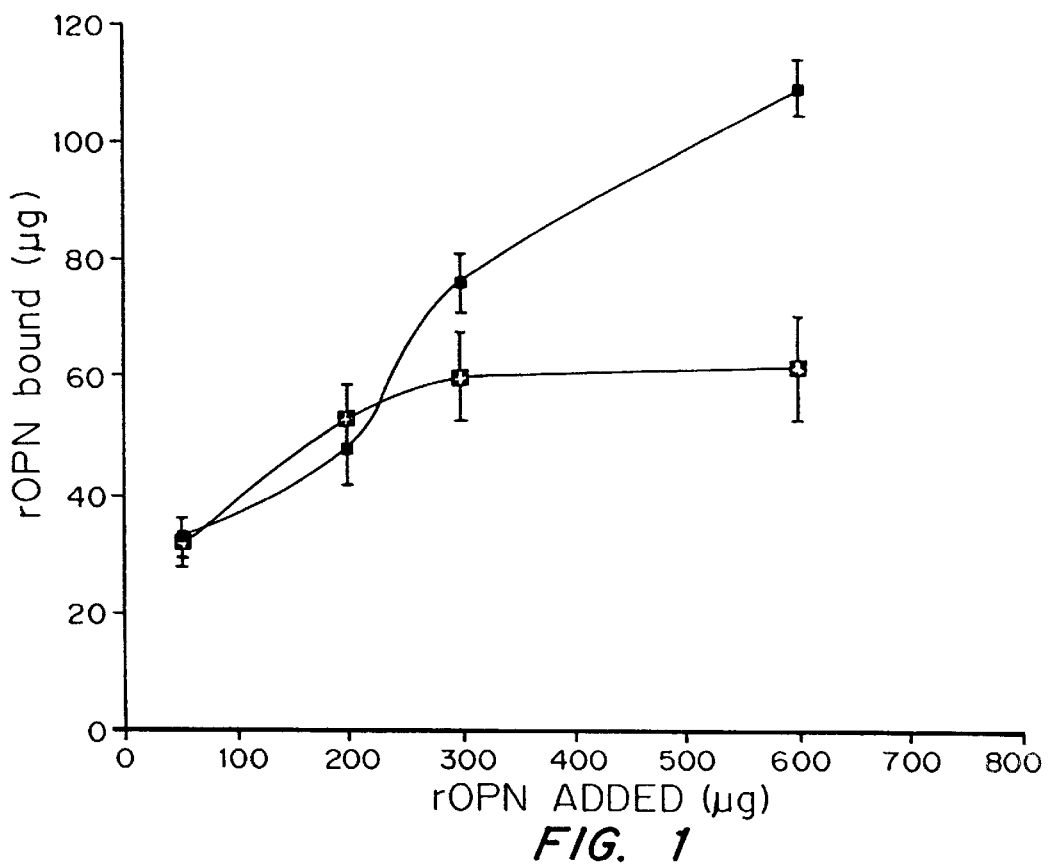

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The present invention is directed to an osteopontin coated implant. The implant includes a material suitable for use in vivo within a subject in combination with a releasable form of osteopontin forming an osteopontin containing implant.

As used herein, the term "material," refers to a material suitable for use in vivo in a subject, e.g., a human or an animal subject, and capable of being part of an implant with osteopontin or a fragment thereof, e.g., releasable osteopontin. There are many art recognized materials suitable for use in vivo. These material include, but are not limited to, titanium, tantalum, Vitallium™, glass, plastic, chromocobalt (CrCo), stainless steel, collagen, cellulose, dextran or teflon beads.

As used herein, the term "osteopontin" or "osteopontin polypeptide," refers to a form of osteopontin or a fragment thereof capable of performing its intended function in vivo, e.g., a form capable of influencing early bone matrix organization and mineralization through a cell, e.g., osteoblast or osteoclast, attachment. Examples of osteopontin forms useful in the invention are: a phosphorylated osteopontin, e.g., an osteopontin having about 6 to about 12 phosphates per mol of protein, preferably, an osteopontin phosphorylated at one or more of the following amino acids selected from the group consisting of Ser26, Ser27, Ser63, Ser76, Ser78, Ser81, Ser99, Ser102, Ser105, Ser108, Ser117, and, preferably Thr138, and most preferably Thr152, a recombinant osteopontin, e.g., a human or murine recombinant osteopontin, e.g., the osteopontin secreted from murine B3H cells, and a naturally occurring osteopontin, e.g., the naturally occurring human osteopontin secreted from human osteoblast cells (SEQ ID NO: 1). In a preferred embodiment threonine 152 is phosphorylated. In a more preferred embodiment, Ser26, Ser27, Ser81, Thr 152 and Ser308 are phosphorylated.

As used herein, the term "active osteopontin peptide," refers to an osteopontin fragment that possesses at least one biological activity of a naturally occurring osteopontin. Preferred peptides include, but are not limited to, chemotactic peptides, e.g., peptides which comprise the amino acid sequence LVLDPK (SEQ ID NO: 2), or LVVDPK (SEQ ID NO: 3), or cell attachment peptides, e.g., peptides which comprise the amino acid sequence RGRDS (SEQ ID NO: 4). In preferred embodiments, the osteopontin peptides can be coated onto the material via covalent, non-covalent, or electrostatic interactions.

Alternatively, a chemotactic peptide can be a peptide which comprises an amino acid sequence X, X', D, Z, Z1, wherein X and X' are hydrophobic amino acids, D is aspartic acid, Z is proline (P), glycine (G), or serine (S), and Z' is a basic amino acid.

Preferred hydrophobic amino acids include asparagine (N), leucine (L), valine (V), isoleucine (I), glutamine (Q), or methionine (M). Preferred basic amino acid residues include lysine (K) and arginine (R). In one embodiment X and X' are selected from the group consisting of L, V, I, Q, M; Z is P, G, or S; and Z' is either K or R. In a most preferred embodiment X is L, X' is L, Z is G, and Z' is K.

Another preferred cell attachment peptide is GRGDS (SEQ ID NO: 5). GRGDS is a cell-binding domain which enhances cell attachment. A preferred cell-binding domain comprises the amino acid sequence VFTPVVPTVD-TYDGRGDSVVYGLRSKSKKFRR (SEQ ID NO: 6).

As used herein, the phrase "in a releasable form," is intended to include osteopontin coated on top of the material in such a way that an osteopontin or a fragment thereof is capable of being released from the surface of the implant and performing its intended function in vivo, e.g., it is capable of establishing an osteopontin gradient in the proximity of an implant, preferably, within about 24 hours, more preferably within about 48 hours, of implantation. As used herein, "osteopontin gradient," refers to a protein gradient which results in the recruitment of cells, e.g., osteoblasts or osteoclasts, to an implant. Preferably, the osteopontin is non-covalently or electrostatically attached to the material. Non-covalent attachment is known in the art and includes, but is not limited to, attachment via a divalent ion bridge, e.g., a Ca++, Mg++ or Mn++ bridge; attachment via absorption of osteopontin or a fragment thereof to the material; attachment via plasma spraying or coat drying of a polyamine, e.g., polylysine, polyarginine, spermine, spermidine or cadaverin, onto the material; attachment via a second polypeptide, e.g., fibronectin or collagen, coated onto the material; or attachment via a bifunctional crosslinker, e.g., N-Hydroxysulfosuccinimidyl-4-azidosalicylic acid (Sulfo-NHS-ASA), Sulfosuccinimidyl(4-azidosalicylamido) hexanoate (Sulfo-NHS-LC-ASA), N-γ- maleimidobutyryloxysuccinimide ester (GMBS), N-γ-maleimidobutyryloxysulfosuccinimide ester (Sulfo-GMBS), 4-Succinimidyloxycarbonyl-α-methyl-α-(2-pyridyldithio)-toluene (SMPT), Sulfosuccinimidyl 6[α-methyl-α(2-pyridyldithio)toluamido]hexanoate (Sulfo-LC-SMPT), N-Succinimidyl-3-(2-pyridyldithio)propionate (SPDP), Succinimidyl 6-[3-(2-pyridyldithio)propionamido] hexanoate (LC-SPDP), Sulfosuccinimidyl 6-[3-(2-pyridyldithio)propionamido]hexanoate (Sulfo-LC-SPDP), Succinimidyl 4-(N-maleimidomethyl)cyclohexane-1-carboxylate (SMCC), Sulfosuccinimidyl 4-(N-maleimidomethyl)cyclohexane-1-carboxylate (Sulfo-SMCC), m-Maleimidobenzoyl-N-hydroxysuccinimide ester (MBS), m-Maleimidobenzoyl-N-hydroxysulfosuccinimide ester (Sulfo MBS), N-Succinimidy(4-iodoacetyl)amino benzoate (SIAB), Sulfosuccinimidyl(4-iodoacetyl)amino benzoate (Sulfo-SIAB), Succinimidyl 4-(p-maleimidophenyl) butyrate (SMPB), Sulfosuccinimidyl 4(p-maleimidophenyl) butyrate (Sulfo-SMPB), or Azidobenzoyl hydrazide (ABH), to the material. In other preferred embodiments osteopontin or a fragment thereof is attached to the material via an electrostatic interaction.

Alternatively, the osteopontin can be attached to an implant for tissue surface via non-covalent attachment, as described above, further including a mucopolysaccharide. Mucopolysaccharides are art recognized and include glycosaminoglycans having, for example, repeating units of N-acetylchondrosine or β1–3 glucuronidic and β1–4 gluconsaminidic groups. Suitable mucopolysaccharides include chondroitin sulfate or hyaluronic acid. Preferably, hyaluronic acid is greater than a disaccharide; the hyaluronic acid has a molecular weight range of less than 100 kDa, more preferably between about 20 to about 100 kDa, e.g. between about 50–100, 70–100, or 30–80 kDa.

As used herein, the term "implant," refers to a surgical implant suitable for use in vivo and where it would be desirable to have osteopontin for promoting cell, e.g., osteoblast or osteoclast, attachment. Examples of suitable implants include but are not limited to dental implants, e.g., dental screws or fixtures, jaw modification implants, face reconstruction implants, orthopedic implants, e.g., orthopedic screws, rods or joints, e.g., hip or knee replacement implants. A preferred implant is a titanium dental implant.

As used herein, the phrase "an osteopontin containing cell recruitment system" refers to a system in which osteopontin or a fragment thereof is introduced into a subject independent of an implant. Preferably, the osteopontin or a fragment thereof is introduced in the proximity of an implant in a form of a gel or a sponge. In other preferred embodiments, the osteopontin or a fragment thereof contained in a gel or a sponge is capable of generating a gradient of osteopontin in the proximity of an implant such that cells, e.g., osteoblasts or osteoclasts, are recruited to the implant. The phrase "an osteopontin containing cell recruitment system" is also intended to include chemotactic effects of osteopontin in facilitating wound healing and stimulating the recruitment of tissue remodeling cells from surrounding tissues. Tissue remodeling cells include mesenchymal, macrophage and granulocytes. Wound healing cells include, for example, cytokines which include TGFB and growth factors, cell-stimulating molecules and healing cells such as macrophages which help to clear chronic necrotic tissue from damaged tissue area.

The term "mesenchymal cell" is art recognized and is intended to include undifferentiated cells found in mesenchymal tissue, e.g., undifferentiated tissue composed of branching cells embedded in a fluid matrix which is responsible for the production of connective tissue, blood vessels, blood, lymphatic system and differentiates into various specialized connective tissues.

The term "growth factors" is art recognized and is intended to include, but is not limited to, one or more of platelet derived growth factors (PDGF), e.g., PDGF AA, PDGF BB; insulin-like growth factors (IGF), e.g., IGF-I, IGF-II; fibroblast growth factors (FGF), e.g., acidic FGF, basic FGF, β-endothelial cell growth factor, FGF 4, FGF 5, FGF 6, FGF 7, FGF 8, and FGF 9; transforming growth factors (TGF), e.g., TGF-β1, TGF-β1.2, TGF-β2, TGF-β3, TGF-β5; bone morphogenic proteins (BMP), e.g., BMP 1, BMP 2, BMP 3, BMP 4; vascular endothelial growth factors (VEGF), e.g., VEGF, placenta growth factor; epidermal growth factors (EGF), e.g., EGF, amphiregulin, betacellulin, heparin binding EGF; interleukins, e.g., IL-1, IL-2, IL-3, IL-4, IL-5, IL-6, IL-7, IL-8, IL-9, IL-10, IL-11, IL-12, IL-13, IL-14; colony stimulating factors (CSF), e.g., CSF-G, CSF-GM, CSF-M; nerve growth factor (NGF); stem cell factor; hepatocyte growth factor, and ciliary neurotrophic factor. Adams et al., "Regulation of Development and Differentiation by the Extracellular Matrix" *Development* Vol. 117, p. 1183–1198 (1993) (hereinafter "Adams et al.") and Kreis et al. editors of the book entitled "Guidebook to the Extracellular Matrix and Adhesion Proteins," Oxford University Press (1993) (hereinafter "Kreis et al.") describe extracellular matrix components that regulate differentiation and development. Further, Adams et al. disclose examples of association of growth factors with extracellular matrix proteins and that the extracellular matrix is an important part of the micro-environment and, in collaboration with growth factors, plays a central role in regulating differentiation and development. The teachings of Adams et al. and Kreis et al. are incorporated herein by reference. The term encompasses presently unknown growth factors that may be discovered in the future, since their characterization as growth factor swill be readily determinable by persons skilled in the art.

As used herein, the phrase "inducing new bone formation," refers to a process which results in attachment, proliferation and/or differentiation of bone cells, e.g., osteoblasts and/or osteoclasts, and subsequent bone mineralization, in the proximity of an implant.

As used herein, the phrase "a coated osseointegrator capable of implantation," refers to a coated material which when implanted into a subject in vivo enhances osseointegration in the vicinity of the coated material by at least about 100% when compared to an uncoated material. Preferably, the coated material is a material coated with an osteopontin or a fragment thereof, as described herein. In other preferred embodiments, the rate of osseointegration is enhanced by at least about 300%, 500%, 800%, 1000%, 1100% or 1200%, when compared to an uncoated material. The percentage values intermediate to those listed also are intended to be part of this invention, e.g., 350%, 875%, or 1150%. Rate of osseointegration can be measured using the human osteoblast cell (HOS) attachment assay as described in Examples 2 and 7 below, or by other methods known to those of skill in the art.

As used herein, the term "coated implant," refers to a coated material which when implanted into a subject in vivo increases the proliferation of osteoblasts in the vicinity of the coated material by at least about 100% when compared to an uncoated material. Preferably, the coated material is a material coated with an osteopontin or a fragment thereof, as described herein. In other preferred embodiments, the rate of proliferation is increased by at least about 50%, more preferably by at least about 200%, when compared to an uncoated material. The percentage values intermediate to those listed also are intended to be part of this invention, e.g., 75%, 125% or 150%. Rate of proliferation can be measured using the human osteoblast cell (HOS) proliferation assay as described in Examples 3 and 8 below, or by other methods known to those of skill in the art.

The present invention is also directed to methods for inducing new tissue formation in a subject at a site where tissue formation is required. The methods include adding osteopontin into a subject at a site where tissue formation is needed, wherein the osteopontin induces new tissue formation about the site. In a preferred embodiment the osteopontin is a recombinant osteopontin. In a most preferred embodiment, the site includes an implant as described herein.

The present invention also pertains to an osteopontin glue. The osteopontin glue includes osteopontin, a mucopolysaccharide and a multivalent metal. Suitable multivalent metals include copper, zinc, barium, calcium, magnesium, and manganese. The osteopontin glue can be administered to an area of tissue in need of repair, e.g., a wound, a cut, or other damaged tissue area, e.g., necrotic tissue. The osteopontin glue can be administered by methods known to those skilled in the art, such as, via injection. Administration of the osteopontin glue enhances tissue regeneration with concomitant removal of necrotic cells. In a preferred embodiment, the osteopontin glue can be used with an implant as described herein.

The osteopontin glues of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Injection or topical application is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The osteopontin glues may be administered to humans and other animals for therapy by any suitable route of administration, including orally, nasally, as by, for example, a spray, rectally, intravaginally, parenterally, intracistemally and topically, as by powders, ointments or drops, including buccally and sublingually.

Regardless of the route of administration selected, the compositions of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredients which are effective to achieve the desired therapeutic response for a particular patient, composition, and mode of administration, without being toxic to the patient.

The selected dosage level will depend upon a variety of factors including the activity of osteopontin of the present invention employed, the route of administration, the time of administration, the rate of excretion of the osteopontin being employed, the duration of the treatment, other drugs, compounds and/or materials used in combination with the osteopontin employed, the age, sex, weight, condition, general health and prior medical history of the patient being treated, and like factors well known in the medical arts. In a preferred embodiment the concentration of osteopontin in the glue is between about 0.1 $\mu$g to about 100 $\mu$g, preferably about 100 $\mu$g/g of carrier.

Not wishing to be bound by theory, it is believed that the osteopontin glue provides a mechanism for "laminating" tissue to tissue or tissue to implant. A plausible explanation for glue's ability to facilitate tissue reconstruction or repair is as follows: Mucopolysaccharides include both hydrophobic and hydrophilic domains, for example, which can coat, e.g., adhere to, the surface of implant or tissue. The mucopolysaccharide provides ionic charge for a multivalent cation to interact with the mucopolysaccharide, acting as a bridge between the implant surface and osteopontin. Once the osteopontin is within the region where cell-recruitment is required, the osteopontin helps to facilitate the regeneration of the tissue in the gradient area of the osteopontin. Alternatively, an implant surface may be oxidized so that the multivalent metal can bind with the oxidized surface, thus providing a bridge directly to the osteopontin. It can be envisioned that interactions between the osteopontin and further layers of mucopolysaccharides can further produce a laminating effect for multiple layers of mucopolysaccharide, multivalent metal, osteopontin.

The osteopontin glue of the invention can further include a pharmaceutically acceptable carrier.

The phrase "pharmaceutically acceptable carrier" is art recognized and includes a pharmaceutically acceptable material, composition or carrier, suitable for administering osteopontin compositions of the invention to mammals by injection. The vehicles include liquid or solid filler, diluent, excipient, solvent or encapsulating material, involved in carrying or transporting the bone precursor composition from a syringe to the cavity in need thereof. Each carrier must be "acceptable" in the sense of being compatible with the other ingredients of the formulation and not injurious to the patient. Some examples of materials which can serve as pharmaceutically acceptable vehicles, include: sugars, such as lactose, glucose and sucrose; starches such as cornstarch and potato starch; cellulose and its derivatives, such as sodium carboxy methylcellulose, ethyl cellulose and cellulose acetate; powdered tragacanth; malt; gelatin; talc; excipients, such as cocoa butter and suppository waxes; oils such as peanut oil, cottonseed oil, safflower oil, sesame oil, olive oil, corn oil and soybean oil; glycol such as propylene glycol; polyols such as glycerin, sorbitol, manitol and polyethylene glycol; esters, such as ethyl oleate and ethyl laurate; buffering agents such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants such as sodium lauryl sulfate and magnesium stearate, as well as coloring agents, stabilizers, preservatives or antioxidants can also be present in the compositions.

Methods of preparing these formulations or compositions include the step of bringing into association the osteopontin glue compositions of the present invention with a carrier and, optionally, one or more accessory ingredients. In general, the formulations are prepared by uniformly and intimately bringing into association the components of the osteopontin glue of the present invention with the carrier.

Liquid dosage forms suitable for administration of the osteopontin glue compositions of the invention include pharmaceutically acceptable emulsions and microemulsions, solutions, suspensions, syrups and elixirs. In addition to the active ingredients, e.g. osteopontin, multivalent metals and mucopolysaccharides, the liquid dosage form can contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propyleneglycol, 1,3-butyleneglycol, oils (in particular, cottonseed, groundnut, corn, germ, olive, castor and sesame oils), glycerol, tetrahydrofuryl alcohol, polyethyleneglycols and fatty acid esters, sorbitan and mixtures thereof.

The osteopontin compositions can also contain adjutants such as preservatives, wetting agents, emulsifying agents and dispersing agents. Prevention of the action of microorganisms may be insured by the inclusion of various antibacterial and anti-fungal agents, for example, paraben, chlorobutanol, phenol sorbic acid, and the like. It may also be desirable to include isotonic agents, sugars, sodium chloride and the like into the compositions. In addition, prolonged absorption of the osteopontin compositions can be brought about by the inclusion of agents which allay absorption such as aluminum monosterate and gelatin e.g., collagen.

In Vitro Modification of Osteopontin

Phosphorylation of Osteopontin

Both natural and recombinant osteopontin can be modified by phosphorylation of the amino acid sequence encoding native osteopontin. The osteopontin can be modified so that phosphorylation is present in the absence of, or with altered glycosylation. The osteopontin can also be modified so that it has less phosphorylation or more phosphorylation than native forms of osteopontin, or is phosphorylated at sites other than those which are naturally phosphorylated.

Phosphorylation is achieved by incubation of the osteopontin in the presence of either eucaryotic kinases such as casein kinase type II or cAMP-dependent kinases. These kinases can be obtained from cytosolic or microsomal extracts, or in purified or semi-purified form from sources such as Sigma Chemical Co., Inc., or as described in the literature. As described in the example below, at least three different kinase preparations from mouse kidney could be used to Phosphorylated osteopontin in vitro. These preparations contain a mixture of kinase activities, several of which can phosphorylate the fusion protein. Casein kinase I, casein kinase II and mammary gland casein kinase participate in hierarchical phosphorylation reactions. Phosphorylation of one site by any of these kinases may affect phosphorylation at another site by a different kinase.

As further demonstrated by the examples below, osteopontin appears to be a complex substrate with at least 58 consensus phosphorylation sites for different types of kinases, as shown in Table I. These putative phosphorylation sites are not randomly distributed throughout the protein but appear as if they were organized in eight clusters. For example, between residues 100 and 126 there are 9 potential phosphorylation sites for either casein kinase I, casein kinase II or mammary gland casein kinase. In addition to potential phosphorylation sites for these independent casein kinase family of enzymes, osteopontin also contains potential phosphorylation sites for cAMP- and cGMP-dependent protein kinases, calmodulin-dependent protein kinase, and protein kinase c. There are several fold more potential phosphorylation sites in recombinant osteopontin than those found phosphorylated in osteopontin isolated from bone. Not all of the potential sites may be phosphorylated at any given time, since some sites may be not accessible to protein kinases or some tissues may not contain all of the kinase activities required for the phosphorylation of osteopontin. Furthermore, the clustering of sites suggests that certain phosphorylated residues can serve as specificity determinants. For example, phosphorylation of a Ser/Thr residue by any kinase can generate a site for phosphorylation of an adjacent phosphorytable residue by either casein kinase I or mammary gland casein kinase. Conversely, phosphorylation at one site by a particular kinase may suppress the phosphorylation of a nearby residue, such as the mutually exclusive phosphorylation of hormone-sensitive lipase by cAMP-dependent protein kinase and calmodulin-dependent protein kinase.

Further modifications on the site and extent of phosphorylation can be achieved by expression of osteopontins with altered structures by differential splicing and post-translational modifications, as well as by the use of fragments and site-specific mutations at any one of these phosphorylation sites.

For phosphorylation by calcium/calmodulin kinase II, the reactions are carried out in the presence of 1.5 mM $CaCl_2$ and 3 $\mu$g calmodulin.

For phosphorylation by protein kinase C, the reactions are carried out in the presence of 8 $\mu$g/ml phosphatidylserine, 0.8 $\mu$g/ml of diacylglycerol, and 1 mM $CaCl_2$.

For autophosphorylation the reaction is carried out in the presence of 10 mM $MnCl_2$.

For phosphorylation by cGMP dependent protein kinase the reactions are carried out in the presence of 0.1 $\mu$M cGMP.

No additions are necessary for the phosphorylation of osteopontin by casein kinase I or mammary gland casein kinase.

Determination of Phosphorylation Sites in Osteopontin

After phosphorylation with $^{32}$P-ATP and the desired kinase, osteopontin is digested with either trypsin, endopeptidase Glu-C, or endopeptidase Asp-N. The resulting peptides are separated by HPLC and the radiolabeled peptides sequenced. The position of the phosphorylated residue is determined by the coelution of radioactivity with the amino acid in that cycle.

Dephosphorylation of Osteopontin

Osteopontin can be dephosphorylated by incubating the protein in either 100 $\mu$l 20 mM HEPES buffer, pH 8.5, and 1 unit of alkaline phosphatase, or 100 $\mu$l 20 mM acetate buffer pH, 5.0 and 1 unit of acid phosphatase, for several hours. Osteopontin can also be dephosphorylated by incubating the phosphoprotein with between 0.1 and 1 units of protein phosphatase 2A at 4° C. for 1 h. Osteopontin can be also dephosphorylated by incubating the protein in 0.1 N NaOH for 1 h at 37° C.

TABLE 1

Predicted phosphorylation sites in Osteopontin

| Protein Kinase | Position of phosphorylated residue |
| --- | --- |
| Casein Kinase I | 239, 275, 280, 308 |
| | 26, 76, 78, 99, 102, 105, 108, 117, 120, 123, 126, 129, 234, 308 |
| Casein Kinase II | 26, 27, 62, 63, 191, 215, 228, 280, 291 76, 237 |
| Ca/Calmodulin-dependent Protein Kinase II | 162, 171 |
| cGMP-Dependent Protein Kinase | 24, 73, 81, 162, 169, 171, 243, 270, 275, 303 |
| cAMP-Dependent Protein Kinase | 224, 243, 270 |
| Protein Kinase C | 49, 239, 171 |
| Tyrosine Kinase | 165 |
| Proline-Dependent Protein Kinase | 147 |

Glycosylation

N-glycosylation of Osteopontin

Osteopontin can be N-glycosylated using colichol-P-P-oligosaccharide and microsomal oligosaccaride transferase. The oligosaccharide side chain can be further processed by using enriched golgi preparations and the appropriate UDP-saccharides.

O-glycosylation of Osteopontin

Osteopontin will be O-glycosylated by incubating the protein with commercially available rabbit reticulocyte lysate, which has been demonstrated by glycosylate nascent proteins in vitro (e.g., Starr, S. M. and Hanover, J. A. (1990) J. biol. chem. 265:6868–6873). Alternatively osteopontin could be O-glycosylated by using purified UDP-GalNAc:polypeptide N-acetylglactosaminyltransferase and UDP-N-acetylgalactosamine. The resulting O-glycosylated protein could be used to build more complex oligosaccharide side chains, using purified transferases and the appropriate sugar derivatives.

Glycation of Osteopontin (Nonenzymatic)

Nonenzymatic glycation involves the condensation of any sugar aldehyde or ketone, including phosphorylated derivatives of sugars, with either an α or ε amino group, resulting first in the rapid formation of a Schiff base. The Schiff base adduct can subsequently rearrange to the more stable Amadoriri product. For example, incubation of osteopontin with glucose, for several hours, will result in the formation β-pyranosyl Schiff base adduct, which will rearrange, with time, to the β-furanosyl Amadori product. Alternatively, the β-pyranosyl Schiff base adduct can be reduced at for 1 h at 22° C. with 0.1% sodium horohydride to yield 1-deoxy-1-aminosorbitol derivative.

Sialation of Osteopontin

O-glycosylated osteopontin can be modified further by the addition of sialic acid. Briefly, 200 µg of osteopontin will be incubated with 0.5 milliunits of β2,3-sialyltransferase in 100 µl 20 mM HEPES buffer pH, 6.5, containing varying concentrations of CMP-sialic acid for 1 h at 37° C. Whereas, N-glycosylated osteopontin can be sialated using α2,6-sialytransferase and the conditions described above.

Deglycosylation of Naturally Occurring Osteopontin

Osteopontin, isolated from tissues, can be deglycosylated by the following methods:

Removal of N-linked Oligosaccharides

After treatment of osteopontin with neuranimidase to remove sialic acids, osteopontin is incubated overnight with 0.3 units of N-glycanase (Genzyme, Boston, Mass.) 100 µl of 20 mM HEPES buffer, pH 7.5, at 37° C.

Removal of O-linked Oligosaccharides

Asialoosteopontin is incubated for 1 to 6 h with 4 milliunits o-glycanase (Genzyme, Boston, Mass.) in 100 µl of 20 mM MOPS buffer, pH 6.0, at 37° C.

Removal of Oligosaccharides from Osteopontin

Total deglycosylation of osteopontin can be achieved by incubating the protein with 0.1% anhydrous trifluoromethanesulphonic acid (TFMS) for several hours. This treatment removes both O- and N-linked oligosaccharides.

Sulfation of Osteopontin

Sulfation of osteopontin and its derivatives is accomplished using the procedure described by Varahabahotla, et al. (1988) BBA, 966:287–296, the teachings of which are incorporated herein, using the enzyme sulfotransferase and 3'-phosphoadenosine-5'-phosphosulfate as the sulfate donor. Osteopontin contains 4 tyrosines. The sulfated proteins are then purified by gel permeation chromatography.

TITANIUM

1 Titanium Surface Characteristics

Titanium (Ti) reacts immediately with oxygen when exposed to air. In less than a millisecond an oxide layer greater than 10A is formed, and within a minute the oxide thickness will be of the order of 50 to 100A (Kasemo B, J. Of Prosth Dent. 49(6):832–837, 1983). Ultrasonic cleaning and autocleaving involves additional growth of the surface oxide, as well as probable incorporation of OH radicals in the oxide (Kasemo B, J. Of Prosth Dent. 49(6):832–837, 1983). Titanium forms several stable oxides such as $TiO_2$, TiO, and $Ti_2O_3$, with $TiO_2$ being the most common one. All oxides have high dielectric constants (higher than for most other metal oxides) in the range of 50 to 120. For these reasons a single stoichiometric oxide is not expected to form on the implant surface. The oxide might be called TiOx, where x gives the average oxygen content of the oxide. The tissue implant reaction is thus a reaction with $TiO_2$ at the implant surface and not with the element titanium as such (Kasemo B, J. Of Prosth Dent. 49(6):832–837, 1983).

Titanium dioxide has physical/chemical characteristics that differ from metallic titanium; characteristics which are more closely related to ceramics than to metals (LeGeros R Z and Craig R G, J. Of Bone and Mineral Research 8(2):s583–s593, 1993). TiO is bioinert, Ti is biotolerant (LeGeros R Z and Craig R G, J. Of Bone and Mineral Research 8(2):s583–s593,1993). Biomaterial composition affects surface chemistry and tissue response. Bioinert materials, which include ceramic oxides (alumina, zirconia)

and biotolerant materials (metal alloys and polymers) do not become directly attached to the bone, and consequently, the material bone interface is weaker in tension and shear strengths but not necessarily in compression loading.

It has been established that titanium oxide surfaces bind cations, particularly polyvalent cations (Abe M., Oxides and hydrous oxides of multivalent metals as inorganic ion exchangers, Inorganic Ion Exchange Materials (ed. A. Clearfield) CRC Press, Boca Raton, Fla., USA, pp 161–273, 1982). Titanium surfaces have a net negative charge at the pH values encountered in animal tissues, the pK being 4.0. This binding of cations is based on electrostatic interactions between titanium-linked 0- on the implant surface, and cations. The oxide layer is highly polar and attracts water and water-soluble molecules in general (Parsegian V A, J. Of Prosth Dent. 49(6):838–841, 1983).

2 The Bone-Titanium Layer

It is known that osseointegrated implants are characterized by the presence of an organic interfacial layer, containing no collagen fibrils, between the bone and the implant. This intervening layer in osseointegrated implants has been reported to stain with lanthanum and alcin blue and is both hyaluronidase and chondroitinase sensitive, suggesting proteoglycan content (Albrektsson T et al, Annals of Biomedical Engineering, 11, 1–27, 1983). The thickness of the glycan layer was found to vary with the biocompatibility of the implant material from 20 to 40 nm for Ti and 30 to 50 nm for zirconia (Albrektsson T, Jacobson M, J. Prosthet Dent 57:597–607, 1987). Establishment of this layer is reported to be critical for the success of the implant since it may provide an optimal interface between the dental implant and the newly formed bone (Nanci A et al, Cells and Materials, 4(1):1–30,1994).

Tissue response to commercially pure Titanium (cp Ti) was examined to characterize the bone implant interface. Lectin cytochemistry was used to detect glycoconjugates and immunocytochemistry for noncollagenous bone and plasma proteins. The composition of the titanium-matrix interface with that of natural bone interfaces such as cement lines and laminae limitantes was compared. The concentration of osteopontin (Opn) and alpha HS-glycoprotein at the bone titanium interface was consistent with the composition of cement lines at matrix-matrix interface and laminae limitantes at various cell-matrix interfaces. Furthermore, the data indicated that the interfacial layer between the bone and the implant is also rich in glycoconjugates containing sacharides such as galactose, a sugar residue found in relatively large proportion in osteopontin.

3 Bone Healing Around Ti

The idea of osseointegration arose from studies of bone wound healing. Titanium chambers containing a transillumination system were inserted into the fibulae of rabbits to observe cellular changes during endosteal wound healing. At the completion of the study, retrieval of the titanium chambers required fracture of bone tissue that was integrated into the chamber surface. This incidental finding became the basis for the use of Titanium in endosseuos implant construction (Branemark P-I, Introduction to osseointegration. In Branemark P-I, Zarb Ga, Aiberktsson T (eds) Tissue-integrated prosthesis. Quintessence Publishing Co, Inc., Chicago, pp 11–76, 1985).

The bone trauma generated by implant placement is followed by clot formation, acute inflammation, recruitment and proliferation of stromal cells and their differentiation into osteogenic lineage cell, followed by filling the defect with and bone and finally mineralization of the matrix (O'Neal RB et al., J. Oral Implantol. 18:243–255, 1992). Throughout this process; macromolecules, including cytokines and adhesion molecules, that orchestrate the course of wound healing and osteogenesis, are secreted into the extracellular milieu (O'Neal et al, Biological requirements for material integration(1992). J. Oral Implantol. 18:243–255, 1992). The interaction of some of these macromolecules with the implant surface determines to a measurable extent how well the implant is integrated.

Early postoperative motion which can occur with an unstable device impairs bone regeneration leading instead for fibrous repair, encapsulation and chronic inflammation, which can further contribute to instability and more excessive motion. If the interface is not integrated, large shear displacements occurring across the interface may result in combined corrosion and wear (Galante J O et al., J. Of Orthopaedic Research. 9:760–775, 1991).

The nature of the implant bone interface is also affected by the surface chemistry and topography of the implant. Since titanium does not induce bone formation, one way of assuring apposition of bone cells to the implant is to design an implant surface that is attractant to these molecules and/or supports osteomorphogenesis.

4 Changes On Macroscopic Characteristics Of Titanium

Steps to maximize integration have addressed the implant: Studies about surface of the implant clearly show that bone cells adhere securely onto Titanium surfaces, and rough-textured (acid) and porous-coated Ti surfaces enhance both the synthesis and mineralization of the extracellular matrix (Bowers K T et al., Int. J. of Oral and Max. Imp. 7(3):302–310, 1992, Groessner-Schreiber B, Tuan R S, J. Of Cell Science 101,209–217, 1992). Electrochemical potentials for porous conditions are relatively similar to those for smooth-surfaced conditions. However, corrosion rates are increased for porous conditions due to the added area per unit volume (Galante J O et al, J. Of Orthopaedic Research. 9:760–775, 1991).

5 Healing Of Bone Using Titanium Coated With Proteins

Recent studies have focused on improving the osseointegration of implants into bone by coating the Ti surfaces of implants with various substances including hydroxyapatite (Klein C P et al., Biomaterials. 15(2): 146–50, 1994; Jansen J A et al., Journal of Biomedical Materials Research. 25(8):973–89, 1991; Holmes R E, Plast. Reconstr Surg 63:626–636, 1979), fibronectin (Rutherford R B et al., International Journal of oral and Maxillofacial implants. 7(3):297–301,1992), and bone morphological proteins (BMP's) (Xiang W et al, Journal of Oral and Maxillofacial Surgery. 51(6):647–511, 993). Histological examinations of bone/titanium interface from such studies revealed various degrees of success in improving the osseointegration of Ti implants.

TITANIUM AND OSTEOPONTIN

1 Protein Expression During Bone Formation

Morphological and histological studies on bone development categorize a linear sequence of cell differentiation progressing from an osteoprogenitor cell to preosteoblasts, osteoblasts and finally osteocytes and lining cells (Aubin J E et al., Analysis of osteoblast lineage and regulation of differentiation. In "Chemistry and Biology of Mineralized Tissue" (H. Slavkin and P Price, eds), pp 267–276. Excepta Medica, Amsterdam, 1992). Recently, the morphological and histological studies have been supplemented with the elucidation of some of the specific proteins secreted by bone cells at specific stages during their development. For example collagen type I is secreted by early and mature osteoblasts but decreases with late osteoblasts and osteocytes. Alkaline phosphatase is expressed by preosteoblasts and is accepted as a marker for osteoblasts. Osteopontin and bone sialoprotein are secreted by early osteoblasts, just prior to the onset of mineralization, but decreases as mineralization proceeds and osteoblasts mature and differentiate into osteocytes. Osteoblastic cells in vitro show an initial peak of Opn mRNA expression at early cultured times, followed by a second mayor peak of expression when the cultures begin to mineralize (Owen T A, J. Cell. Physiol. 143, 420–430, 1990; Strauss G P et al., J. Cell. Biol. 110,1368–1378, 1990). Osteocalcin is secreted by mature osteoblasts after the onset of mineralization. The order of appearance of proteins at bone interfaces, particularly with respect to type I collagen, is important in understanding the events leading to bone formation and turn over, and ultimately osseointegration.

2 Possible Role of Osteopontin In Bone Formation

Osteopontin is a cell adhesion protein first identified in bone, but now associated with other tissues as well. Osteopontin is a phosphorylated glycoprotein containing an RGD cell-binding sequence. In mineralized tissues, OPN is expressed prior to mineralization and regulated by osteotropic hormones, binds to hydroxyapatite, and enhances osteoclast and osteoblast adhesion. Although the exact function of Opn is yet unknown, possibilities include a role in the recruitment of bone precursor cells to a site of mineralization, and a role in protection against bacterial infection (Butler W T, Connect. Tissue Res. 23,123–136, 1989).

Osteopontin in laminae limitantes at bone surfaces may act as a substrate for osteoclast adhesion, and then for initial sealing zone attachment, during osteoclast migration and bone matrix resorbtion, respectively. During the reversal phase of the remodeling sequencing, the initial expression of osteopontin has been suggested to reflect the involvement of this noncollagenous bone protein in cell-matrix interaction (Lian J B, Stein G S, Crit. Rev. Oral Biol. Med. 3, 269–305, 1992). Opn secreted early in the life cycle of differentiating preosteoblasts accumulates at the resorbed bone surfaces to form a cement line. The deposition of this planar arrangement of Opn initially may serve to influence early matrix organization and mineralization, and possibly preosteoblasts adhesion at these sites. It also may function in a broader sense as a matrix-matrix/mineral biological glue to attach newly formed bone to older bone in order to maintain overall tissue integrity and biomechanical strength during bone remodeling (McKee M D, Nanci A, Osteopontin and the bone Remodeling Sequence—Colloidal-Gold Immunocytichemistry of an Interfacial Extracellular Matrix Protein, In: Osteopontin:Role in Cell Signaling and Adhesion. Annals of the New York Academy Sciences 760: Apr. 21, 1995). Based on the sequence of appearance of matrix proteins, it may be postulated that Opn place a dual role, first participating in cells attachment and then in the mineralization of the cement line-like material found in vivo (Shen X, Cells and Materials 3, 257–272, 1993).

3 Bonding of Proteins to Titanium Surfaces

An implanted material attains and maintains contact with interfacial tissue through its surface. When a substrate or an implant is inserted into the body environment, it is exposed to cells and a host of ionic and molecular species that ultimately determine the course of interfacial events (Kasemo B, J. Of Prosth Dent. 49(6):832–837, 1983). One of the first things to happen is the absorption of proteins onto the substrate (Kasemo B, J. Of Prosth Dent. 49(6):832–837, 1983). The absorption takes place within the first 10 to 60 seconds of contact, long before the cells get access to the surface. This means that any cells which interact with the alloplast surface can only do so indirectly, through the absorbed protein layer.

The nature and amount of protein absorbed is specific to the alloplast composition (Uniyal S, Brash J L, Thromb. Haemost. 47, 285–290, 1982), depending on the physical and electromechanical properties of the given surface. It is conceivable that the absorbed protein contingent could determine what kind of cells interact with the alloplast surface (Bagambisa F B et al., Int. J. Oral Maxillof Implants 5, 217–226, 1994). Cell contact with the substrate is maintained by the formation of subcellular spatially and morphologically defined adhesion sites called focal adhesions. Focal adhesion are within 15 to 30 nm proximity of the substrate (Izzard C S, Lochner R L, J. Cell Sci. 21:129–159, 1976) and are about 2 to 10 $\mu$m long and 150 to 500 nm wide (Burridge K et al, Ann. Rev. Cell Biol., 487–525, 1988). Although the different phenomenological response of cells to material surfaces has been attributed to wetability, this can only be a first approximation (Parsegian V A, J. Of Prosth Dent. 49(6):838–841, 1983). It appears more useful to talk about the ability of the surfaces to interact with the key molecules involved in the orchestration of the post implantation interfacial events. If a material surface can not bind the macromolecules supportive of osteoblast function, the material is not likely to make a good bone implant. One way of getting bone cells to appose bone tissue onto the implant surface might be through having or creating surfaces that are attractant to the macromolecules responsible for events like cell phenomenology, growth and differentiation (Bagambisa F B et al. Int. J. Oral Maxillof. Implants 5:217–226, 1994).

The absorption onto Ti of aqueous solutions of matrix or matrix-like proteins has resulted in significant increases in the number of cells bound. This effect has been reported (Burridge K et al. Ann. Rev. Cell Biol. 487–525, 1988) and indicates that a specific cell receptormatrix protein interaction is a more efficient means of attachment than the undefined process of cell-Ti interaction.

Histological information is available on the interface between bone and implant material, but the understanding of the mechanisms operating when an implant is inserted into bone is limited and the concepts are speculative.

The process of integration is going on in an aqueous environment. When two bodies make contact, it is because they prefer each other to the intervening water or whatever else is originally between them. In the vicinity of an electrical charge, a molecule will turn to keep its attractive end close to the intruding charged body (Parsegian V A, J. Of Prosth Dent. 49(6):838–841, 1983). Small amounts of positively charged calcium ion will bind to certain electrically negative surface groups, displacing the water and replacing it with a bridge of (−) (+), (+) (−) configurations between bilayers. Expotentionally decay repulsion seen between bilayer membranes is seen also between single molecules (Parsegian V A, J. Of Prosth Dent. 49(6):838–841, 1983).

There are two paths in which a range of close interaction can be analyzed: first, the list of hydrogen bonds, hydrophobic bonds, salt bridges, van der Waals forces. Second, direct inspection of molecular contacts are they occur in protein monomers or tetramers the structures of which have been determined to atomic resolution by x-ray diffraction.

The metal surface is in fact a highly polarizable titanium oxide layer probably modified by accumulated impurities, from the bulk metal phase. Whit time, the titanium with oxide surface blends with material from adjacent tissue, and a thin layer of ground substance of cellular origin is deposited on the implant so as to cement bone tissue and titanium. The interactions of principal importance probably are electrostatic rather than van der Waals or hydrophobic interactions (Parsegian V A, J. Of Prosth Dent. 49(6):838–841, 1983). To a charged body, the highly polar oxide layer provides a strongly attractive alternative to water. The many configurations of titanium and oxygen likely to occur in such a surface provide a wide variety of adsorbant sites to attract various arrays of charge that probably reside on the water-soluble ground substance.

The oxide layer is so highly polar and therefore able to attract species that are ordinarily water soluble. Positive electrical charges in particular will move toward the oxide, for in addition to its polarizability the layer is negatively charged. It should not be surprising that such a highly polar region has been observed to incorporate (positive) calcium and (negative) phosphate ions from the adjacent aqueous phase. It is almost certain that the polar properties of adsorbant and substrate—not van der Waals forces, nor generalized electrical doubled layer, nor hydrophobic attractions—will determine contact (Parsegian V A, J. Of Prosth Dent. 49(6):838–841, 1983).

The chemical property of the titanium oxide surface suggests that calcium ions may be attracted to the oxide cover surface by electrostatic interaction with O- as just discussed. Calcium deposits have been observed in direct contact with the titanium oxide (Albrektsson T, and Hansson H A, Biomaterials, 7,201–205, 1986). According to the same model, calcium binding macromolecules may absorb selectively to the implant surface in vivo as the next sequence of events. Calcium binding molecules are often acidic with surface exposed carboxyl, phosphate or sulphate groups. Proteoglycans and/or proteins containing carboxyl and phosphate/sulphate groups may bind to the $TiO_2$ surface by this mechanism. Hydroxyapatite, the major mineral component of bone, also exhibits a surface dominated by negatively charged oxygen (P-bound) that can attract cations and subsequently anionic calcium binding macromolecules (Bernardi G and Kawasaki T, T: Chromatography of polypeptides and proteins on hydroxyapatite columns, Biochim. Biophys. Acta. 160, Pp 301–310, 1968). Glycosaminoglycans interact electrostatically with hydroxyapatite surface (Embery G and Rolia G, Interaction between sulphated macromolecules and hydroxyapatite studied by infrared spectroscopy. Acta Odontol. Scand, 38, 105–108, 1980). It has been shown that calcium absorbs to the surfaces after treatment with $CaCl_2$. The absorption of calcium onto the titanium implant surface when exposed to body fluids, increase its biocompatibility with bone and induce a subsequent adsorption of calcium binding macromolecules on to the implant surface. The surface characteristics of $TiO_2$ probably change from an anionic to a cationic state by the adsorption of calcium to the surface which will be subsequently have an increased ability to absorb acidic macromolecules like Opn. The results of the study were consistent with the proposal that calcium binding is a major mechanism by which proteins adsorb to $TiO_2$.

The present invention is further illustrated by the following Examples which in no way should be construed as further limiting. The entire contents of all of the references (including literature references, issued patents, and published patent applications) cited throughout this application are hereby expressly incorporated by reference.

EXAMPLES

Titanium, plastic, glass and chromocobalt (CrCo) surfaces were coated with human recombinant OPN. Attachment and proliferation of human osteoblasts by means of matrix formation markers was evaluated using uncoated surfaces as a control. Also the amount of adhesion protein that can be coated to these surface was investigated.

The human recombinant phosphorylated form of osteopontin (rhOpn) was used as an adhesion molecule. This form of osteopontin migrates on 10% SDS-gels with an apparent molecular weight of 78 Kd, making it easy to differentiate from osteopontin secreted by osteoblasts which migrates in the same gels with an apparent molecular weight of 58 Kd.

The experiments outlined below investigate the expression and mineralization of extra cellular matrix components in human osteoblasts cultured on titanium disks, plastic, glass and chromocobalt surfaces coated with recombinant osteopontin. The adhesion molecule rhOPN used as a coating for these surfaces enhances attachment and proliferation of human osteoblasts cell lines, and increases the expression of matrix components when compared against uncoated surfaces.

MATERIALS AND METHODS

Cell Culture of Human Osteoblasts 50,000 cells from the human osteoblastic cell line were seeded onto sterile titanium disks (11 mm in diameter) or titanium disks coated with recombinant Osteopontin placed inside a 24 well plate (12 mm diameter well) (Costar, Cambridge, Mass.). Cells were initially maintained in Dulbecco's Modified Medium (DME) supplemented with 10% fetal bovine serum until reaching confluence. The cells were then grown in DME media supplemented with 10% fetal bovine serum, 12.5 ug/ml ascorbic acid and 5 mM B-glycerophosphate (denoted as complete media).

Determination of Protein Absorption onto Titanium Surfaces

Titanium disks were cleaned in 10% Nitric acid for 12 hours, washed exhaustively with water, sterilized, then placed inside a 24 well plate (12 mm diameter well) (Costar, Cambridge, Mass.), and washed twice with 0.5 ml of sterile PBS. 0.1 milimolar $CaCl_2$ was added to 8 disks. Four different concentrations of the human recombinant osteopontin (60, 200, 400, 600 ug) were labeled with S35, and placed on all the titanium disks. After 24 hours, the bound and unbound protein was collected and counted using the Scintillation counter (Bergman 5000). The values among the two groups at the four concentrations were compared to determine the action of Calcium as a binding agent and the adequate concentration of the recombinant protein.

The Attachment of HOS Cells as a Function of the Substrate They Were Grown On HOS cells were labeled overnight with 10 uCi $^3$H-thymidine, then dissociated from the plate with non-enzymatic dissociation solution (Sigma), washed 2 times with PBS, and counted. $^3$H-thymidine incorporated into TCA insoluble material was determined for the cells. 5000 cells (cpm total 1000) were plated onto coated or uncoated titanium disks and the disks incubated at 37° C. for 30 min. Unadhered cells were removed, and attached cells were washed 3 times with 0.5 ml PBS. The cells were lysed with ice cold 20% TCA and the radioactivity in the TCA insoluble fraction was determined using the Scintillation counter (Begman 5000).

The Proliferation of HOS Cells as a Function of the Substrate They Were Grown On Cell proliferation was determined by the rate of $^3$H-Thymidine incorporation into DNA. Cells were labeled with 10 uCi/ml of $^3$H-Thymidine in DME media. After 6 hours, the cells were lysed in cold 10% trichloroacetic acid (TCA). The TCA insoluble material was collected and washed several times with 10% TCA, then resuspended in 0.5 N NaOH. $^3$H-thymidine incorporation into TCA insoluble material was used as an index of cell proliferation. The material collected was mixed with scintillation liquid (Begman). The amount of radiation generated was compared between cells grown in titanium disks uncoated, and titanium disks coated with OPN.

Synthesis of Osteopontin (Opn) and Bone Sialoprotein (BSP), and Their Secretion and Deposition into the Extracellular Matrix Osteopontin and BSP were extracted from the extracellular matrix of HOS cells cultured on Ti disks or Ti disks coated with the recombinant Opn with lysis buffer (20 mM phosphate buffer, pH, 7.2, containing 150 mM NaCl, 0.1% SDS, 1 mM phenylmethylsulfonyl fluoride, 5 mM benzamidine, 0.1 mM e-amino caproic acid, 0.1 b-hydroxy mercuribenzoate, 0.1 mM pyrophosphate, 1 mM sodium fluoride, 1 mM sodium orthovanadate and 10 mM EDTA). Samples were then processed for Gel electrophoresis.

Western Blot Analysis

Cell layer proteins and conditioned media was electrophoresed in 10% SDS-polyacrylamide slab gels at 150 volts for 4 h. For Western blot analysis resolved proteins in gels were transferred by semi-dry blotting onto nitrocellulose membranes (Schleicher & Schuell, Keene, N H), gel transfers were carried out for 90 min. at 12 V in 0.025 M Tris-glycine buffer, pH 8.2, containing 20% methanol and 0.01% Tween 20 and 10% nonfat dry milk, then incubated with rabbit anti-mouse osteopontin (Ashkar S, et al., New York Academy of Science 760:296–298, 1995) in 20 mM Phosphate buffer, pH 7.4, containing 150 mM NaCL, 0.1% Tween 20 and 1% nonfat dry milk. After 1 h, the membranes were washed 3 times with 20 mM Phosphate buffer, pH 7.4, containing 150 mM NaCl, 0.1% Tween 20, then incubated with horseradish peroxidase-conjugated goat anti-rabbit 1 g antibodies for1 h. Following several washing steps, the membranes were developed with ECL. Nonspecific interaction was assessed by the interaction of the primary and secondary antibodies with rabbit serum albumin.

Identification of proteins was made running the samples collected in a 7.5% SDS-polyacrylamide slab gels at 150 volts for 4 h. Then, the gels were stained by immersion in Coomassie blue for 24 hours. The gel was washed with 10% Acetic Acid, 20% Methanol, 70% ddWater, and the proteins identified by molecular weight against the standards ran with the samples.

The Expression of Alkaline Phosphatase Enzyme Activity on Human Osteoblast Cell Membranes in Culture Alkaline phosphatase enzyme activity was determined in glycine buffer pH 10.2 using p-nitrophenol phosphate as described (Gerstenfeld L C et al., Develop Biol; 122:4940, 1987). Briefly, cell layer was extracted with NP 40 (Detergent) in PBS for 10 min. at 4° C. 100 I$\mu$l Aliquots were frozen until used. Then, the samples were thawed and prepare in glycine buffer plus p-nitrophenol phosphate for one hour at 37° C. After the samples turned yellow, the reaction was stopped with 0.2 milimolar Na OH, and the samples were read in the spechtometer (Begmann).

Determination of Mineral Content of Human Osteoblast Cell Culture

HOS cells were grown either on coated or uncoated titanium disks. Media was supplemented with ascorbate and b-glycerol phosphate to stimulate the mineralization of the extracellular matrix. After two weeks, media was removed and the cells were lysed with triton. Then, all soluble components were removed and calcium content was determined using quantitative, colorimetric determination at 575 nm (Sigma Diagnostics Calcium). Basically, calcium reacts with o-cresolphthalein, a chromogenic agent that in an alkaline medium forms a purple colored complex. The intensity of the color, measured at 573 nm, is directly proportional to calcium concentration in the sample.

Example 1

Effect of Ca++ ions on the Binding of Osteopontin to Ti Disks

Increasing concentration of 35S-labeled OPN (60, 200, 400, 600 ug) were incubated with titanium disks either with (■) or without (+) CaCl$_2$ at 4° C. After 24 h the unbound protein was removed and the Ti disks were washed with PBS. Bound OPN was extracted from the disks with scintilation fluid and counted. Each experiment was done in triplicates and reported as mean±SEM.

To investigate whether exogenously added Ca++ had any effect on the binding of rhOPN to Ti, the binding of rhOPN to Ti disks was measured with and without added CaCl$_2$. The results, presented in FIG. 1, demonstrate that in the absence of added CaCl$_2$ the Ti disks saturate at 60 $\mu$g of rhOPN, but in the presence of 100 mM CaCl$_2$ the Ti disks can bind more rhOPN saturating at more than 110 $\mu$g protein/disks.

Example 2

Attachment of HOS Cells to Ti Surfaces Coated with rhOPN 5000 cells (total cpm 1000) were plated on either coated or uncoated Ti disks and incubated at 37° C. in a humidified atmosphere (95% air 5% C0$_2$). After 30 min, unattached cells were removed and the disks were washed with PBS. The total number of attached cells was determined for the total cpm released for the disks after the cells were lysed with 10% TCA and solubilized in 5 ml scintillation fluid. All measurements were done in triplicates and graphed as mean±Standard error of the mean.

Figure 2:
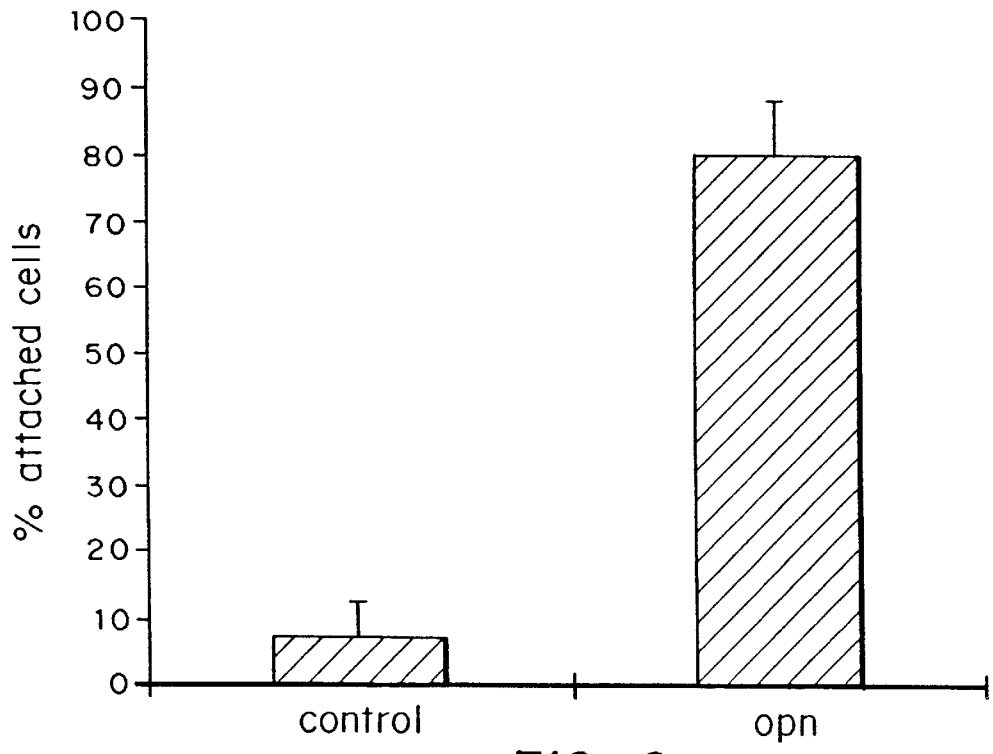
FIG. 2 is a bar graph depicting the effect of rhOPN on cell attachment to Titanium.

The initial events following seeding of cells onto Ti surfaces include the attachment, migration and proliferation of the seeded cells. Coating Ti disks with 50 $\mu$g of rhOPN enhanced by 1100% the attachment of HOS cells to Ti disks (FIG. 2), after 30 min. These results are consistent with the role of osteopontin in promoting cell attachment and spreading.

Example 3

Proliferation of HOS Cells on Ti Surfaces Coated with Phosphorylated Human Recombinant Opn Cell proliferation was determined by the rate of $^3$H-Thymidine incorporation into DNA. Cells labeled with $^3$H-Thymidine were seeded for 6 hours, then lysed with TCA. The TCA insoluble material was collected and resuspended in 0.5 N NaOH. $^3$H-thymidine incorporation into TCA insoluble material was used as an index for cell proliferation. Rate of proliferation is expressed as cpm/1000 cells/6 h. Control group: 254,54, rhOPN group: 560,83. All measurements were done in triplicates and reported as mean±Standard error for the mean.

Figure 3:
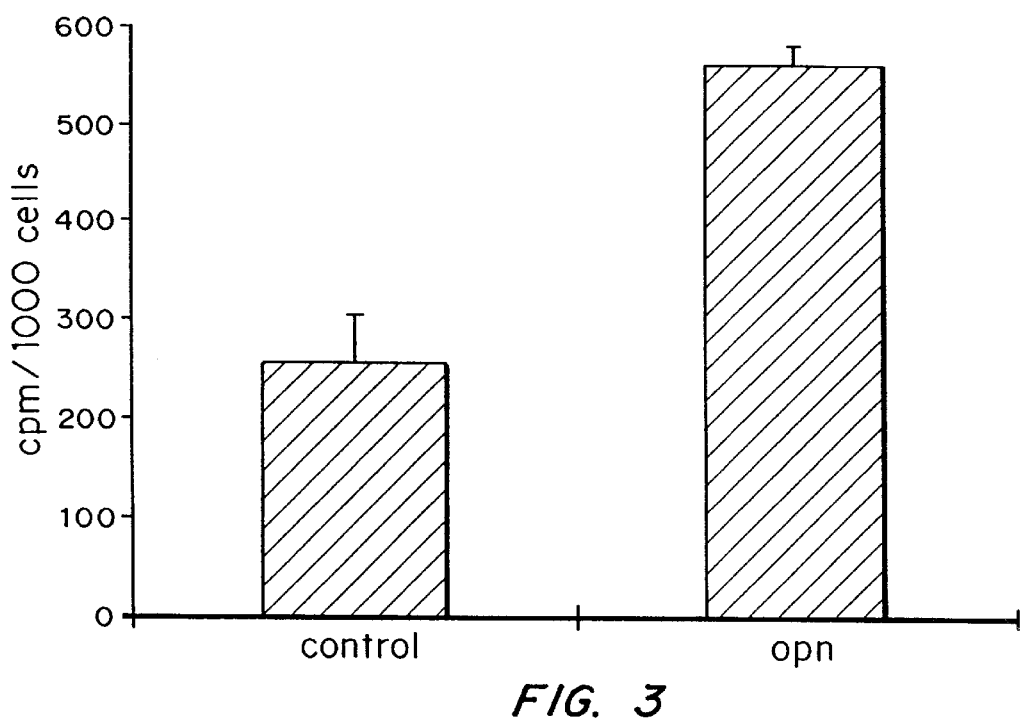
FIG. 3 is a bar graph depicting the effect of rhOPN bound to Titanium on cell proliferation.

Since rhOPN promoted cell attachment to Ti disks, it was of interest to examine whether the protein had any effect on the proliferation of HOS grown on Ti disks. Measurement of the rate of proliferation of HOS cells grown on coated or uncoated Ti disks showed that the proliferation rate of cells grown on rhOPN coated Ti disks was approximately twice (FIG. 3) the proliferation rate of cells grown on uncoated Ti disks.

Example 4

Secretion of Osteopontin and BSP by HOS Cells Growing on Coated Ti Disks

Cell layer proteins and conditioned media was electrophoresed in 10% SDS-polyacrylamide slab gels at 150 volts for 4 h. The resolved proteins were transferred by semi-dry blotting onto nitrocellulose membranes for 90 min. at 12 V in Transfer Buffer. Then, the membranes were incubated with either rabbit anti-mouse osteopontin or rabbit anti-mouse BSP. After 1 h, the membranes were washed 3 times with PBST. Then incubated with horseradish peroxidase-conjugated goat anti-rabbit Ig antibodies for 1 h. Following several washing steps in PBST, the membranes were developed with ECL as described by the manufacturer (Amersham, London).

Osteopontin and BSP were extracted from the extracellular matrix of HOS cells cultured on Ti disks or Ti disks coated with the recombinant Opn with lysis buffer. Samples were then processed for Gel electrophoresis. Western blot analysis for OPN secretion into the extracellular matrix showed increased secretion of OPN from cells grown on coated Ti disks when compared to cells grown on uncoated titanium controls as denoted. Assays for Opn expression by Western blot were done by triplicate.

BSP extracellular matrix secretion expressed by Western blot analysis was less marked than the production of osteopontin from cells grown on the rhOPN coated implants. Cells in the control groups did not expressed bone sialoprotein. Assays for BSP expression by Western blot were done by triplicate.

Example 5

Expression of Alkaline Phosphatase Enzyme Activity on Human Osteoblast Cell Membranes in Culture Alkaline phosphatase enzyme activity was determined in glycine buffer pH 10.2 using pnitrophenol phosphate. Cell layer was extracted with NP 40 in PBS for 10 min. at 4° C. 100 μl Aliquots were used. The alkaline phosphatase activity determined by colorimetric assay (as described in materials and method). A unit is defined as the amount of enzyme which releases 1 umol of p-nitrophenol/h. All measurements were done in triplicates and reported as mean±Standard error of the mean.

Figure 4:
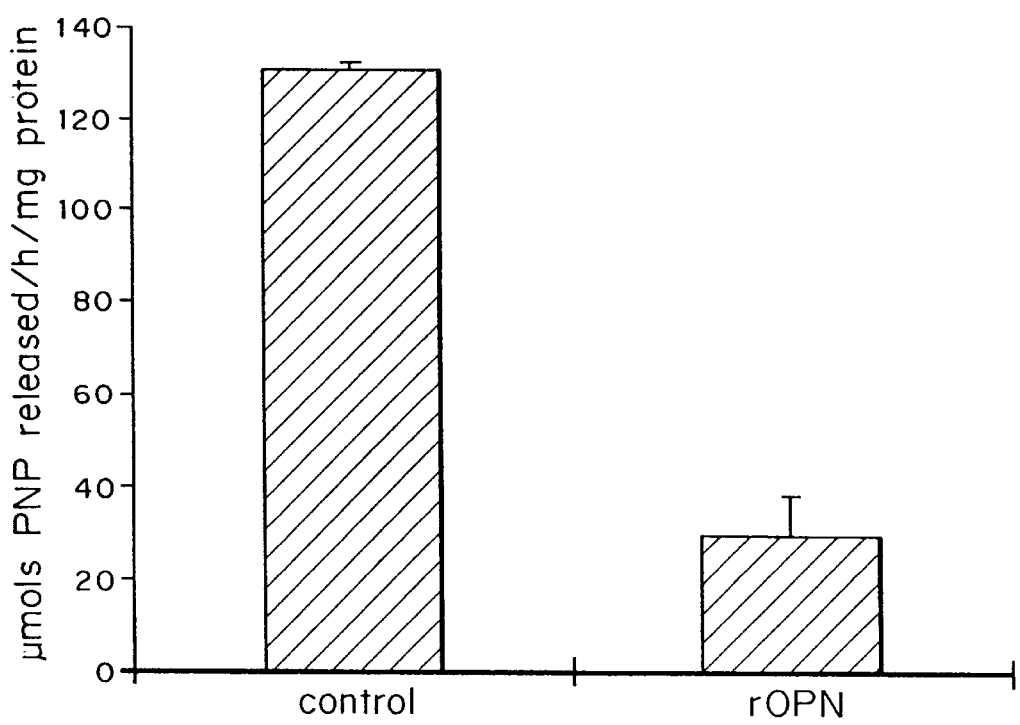
FIG. 4 is a bar graph depicting Apase activity of cells on coated and uncoated Titanium.

Since secreted proteins and extracellular matrix production was different between cells grown on coated and uncoated disks, the levels of alkaline phosphatase in both groups were examined to assess the extent of differentiation of HOS cells grown on coated Ti Surfaces. The results presented in FIG. 4, indicate that the levels of alkaline phosphatase activity in cells grown on Ti disks decreased over the levels of Apase detected in the control groups. These results are consistent with the observations that Apase activity decreases as osteoblasts differentiate into mature matrix producing cells.

Example 6

Extracellular Matrix Mineralization of HOS Cells Grown on Either Coated or Uncoated Ti HOS cells were grown either on coated or uncoated titanium disks. Media was supplemented with ascorbate and β-glycerol phosphate. After two weeks, media was removed and the cells were lysed. Then, all soluble components were removed and calcium content was determined using quantitative, calorimetric determination at 575 nm (Sigma Diagnostics Calcium). All measurements were done in triplicates andreported as mean±Standard error in the mean.

Figure 5:
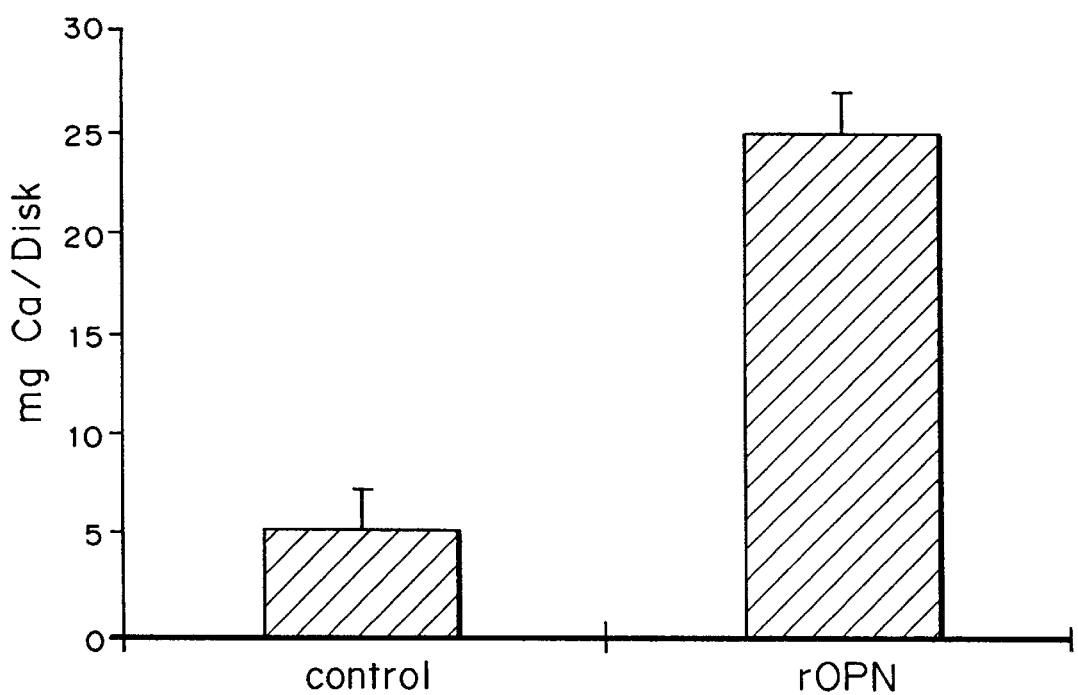
FIG. 5 is a bar graph depicting mineral content of human osteoblast cell culture.

When cultured in the presence of ascorbate and β-glycerol phosphate, HOS cells grown on coated Ti disks mineralized their extracellular matrix within 2 weeks (FIG. 5) in a manner similar to HOS cells cultured on plastic. However, HOS cells grown on uncoated Ti disks under similar conditions did not mineralize their extracellular matrix. These results and the results presented above suggest that when cultured on uncoated Ti disks HOS cells attach, proliferate and differentiate at a slower rate than when cultured on coated disks. Furthermore, HOS cultured on coated disks synthesize an extracellular matrix that mineralizes within two weeks. In several respects HOS cells grown on Ti surfaces coated with rhOPN develop in a manner similar to cells grown on plastic dishes.

Example 7

Attachment of HOS Cells to Surfaces Coated with OPN 500 cells were plated on coated plastic, glass or chromocobalt surfaces and incubated at 37° C. in a humidified atmosphere (95% air 5% $CO_2$). Surfaces were coated with either human recombinant phosphorylated OPN (rhOPN) or unphosphorylated OPN. Fibronectin coated surfaces were used as a control. After 1 hour, unattached cells were removed and the surfaces were washed with PBS. The total number of attached cells was determined for the total cpm released for the surfaces after the cells were lysed with 10% TCA and solubilized in 5 ml scintillation fluid. All measurements were done in triplicates. The results are outlined in Table 2 below.

TABLE 2

| Surface | % total attached |
|---|---|
| plastic | |
| OPN | 43.6 |
| OPN-p | 90.8 |
| fibronectin | 91.6 |
| glass | |
| OPN | 37.2 |
| OPN-p | 98.1 |
| fibronectin | 89.6 |
| chromocobalt (CrCo) | |
| OPN | 4 |
| OPN-p | 69.2 |
| fibronectin | 54.8 |

OPN = unphosphorylated OPN
OPN-p = phosphorylated OPN

The results outlined above demonstrate that human recombinant phosphorylated OPN (rhOPN) promoted cell attachment at the same or higher rate then fibronectin. These results are consistent with the role of osteopontin in promoting cell attachment and spreading.

Example 8

Proliferation of HOS Cells on Surfaces Coated with Phosphorylated Human Recombinant Opn Cell proliferation was determined by the rate of $^3$H-Thymidine incorporation into DNA. Cells labeled with ³H-Thymidine were seeded for 6 hours, then lysed with TCA. The TCA insoluble material was collected and resuspended in 0.5 N NaOH. ³H-thymidine incorporation into TCA insoluble material was used as an index for cell proliferation. Rate of proliferation is expressed as cpm/1000 cells/6 h. All measurements were done in triplicates.

Since rhOPN promoted cell attachment to different surfaces, it was of interest to examine whether the protein had any effect on the proliferation of HOS grown on these surfaces. Measurement of the rate of proliferation of HOS cells grown on coated or uncoated glass, plastic and chromocobalt surfaces showed that the proliferation rate of cells grown on rhOPN coated surfaces was at least twice (Table 3) the proliferation rate of cells grown on uncoated surfaces.

TABLE 3

| Surface | Proliferation Rate (Rate Cpm/6 h/1000 cells) |
|---|---|
| Plastic only | 1100 |
| Plastic + rhOPN | 3300 |
| Glass only | 310 |
| Glass + rhOPN | 2740 |
| CrCo only | 120 |
| CrCo + rhOPN | 1740 |

Example 9

In Vivo Studies of Ti Coated rhOPN Implants

Forty implants (5 per quadrant) were placed in four Haundel/Labrador dogs after extraction of four premolars (PM1-PM4) and one molar (M1), and a three month healing period. Eight hollow screw Ti implants were coated with rhOPN. Eight uncoated implants served as controls. The remaining implants were coated with 3 additional different molecules denoted as study 2, study 3, and study 4.

Prior to implant placement, core samples from the donor place were taken to histologically analyze bone quality after extractions. This procedure, also ensured a hollow space for bone ingrowth inside the coated and uncoated implants. Dogs were sacrificed after 4 and 8 weeks.

Implants were recovered for histological analysis. Each implant was sectioned vertically. The core inside the hallow implant was removed using liquid nitrogen. Decalcified sections were embedded in paraffin and stained using Herovichi's techniques to differentiate immature from mature collagen. Light microscopy at 4× and 40× magnifications were used to compare histological differences between rhOPN coated implants and uncoated implants.

The in vivo results show enhanced bone healing around coated implants. Uncoated implants show normal bone healing characterized by granulation tissue and a few areas of vascularization and matrix deposition after four weeks. These results demonstrate that coating titanium implants with rhOPN reduces healing time around dental implants.

The results outlined above demonstrate that coating of different surfaces, e.g., titanium disks, glass, plastic, or CrCo, with phosphorylated human recombinant osteopontin enhances the rate of attachment and proliferation of human osteoblast cell lines in vitro when compared to uncoated surfaces. This enhancement is demonstrated by better attachment and proliferation of the cells, increased production of the extracellular matrix components, and its faster calcification. These results also contribute to the understanding of the molecular events that may be occurring in the healing of bone around the implants.

Equivalents

Those skilled in the art will be able to recognize, or be able to ascertain using no more than routine experimentation, numerous equivalents to the specific procedures described herein. Such equivalents are considered to be within the scope of this invention and are covered by the following claims.

What is claimed is:

1. An isolated active osteopontin peptide derived from osteopontin comprising the amino acid sequence VFTPVVPTVDTYDGRGDSVVYGLRSKSKKFRR (SEQ ID NO:6).

2. The peptide of claim 1 comprising the amino acid sequence VFTPVVPTVDTYDGRGDSVVYGLRSKSKKFRR (SEQ ID NO:6) immobilized to a substrate.

3. The peptide of claim 1 consisting essentially of the amino acid sequence VFTPVVPTVDTYDGRGDSVVYGLRSKSKKFRR (SEQ ID NO:6).

4. A coating comprising an active osteopontin peptide comprising the amino acid sequence VFTPVVPTVDTYDGRGDSVVYGLRSKSKKFRR (SEQ ID NO:6).

5. An implant having bound thereto an active osteopontin peptide derived from osteopontin comprising the amino acid sequence VFTPVVPTVDTYDGRGDSVVYGLRSKSKKFRR (SEQ ID NO:6).

6. The coating of claim 4 wherein the peptide consists essentially of the amino acid sequence VFTPVVPTVDTYDGRGDSVVYGLRSKSKKFRR (SEQ ID NO:6).

7. The coating of claim 4 wherein the coating is an a prosthetic or implant.

8. The coating of claim 4 wherein the coating is on a substrate for attachment of cells.

9. The coating of claim 4 wherein the coating is on a substrate selected from the group consisting of titanium, tantalum, vitallium, plastic, glass, stainless steel, collagen, cellulose, dextran, tetrafluoroethylene and chromocobalt.

10. The coating of claim 4 wherein the coating is on a substrate selected from the group consisting of titanium, tantalum, vitallium, plastic, glass, stainless steel, collagen, cellulose, dextran, tetrafluoroethylene and chromocobalt.

11. The implant of claim 5 wherein the peptide is dispersed in a coating on the surface of the implant.

12. The implant of claim 5 wherein the peptide consists essentially of the amino acid sequence VFTPVVPTVDTYDGRGDSVVYGLRSKSKKFRR (SEQ ID NO:6).

* * * * *

SEQUENCE LISTING

<160> NUMBER OF SEQ ID NOS: 6

<210> SEQ ID NO 1
<211> LENGTH: 314
<212> TYPE: PRT
<213> ORGANISM: Homo sapiens

<400> SEQUENCE: 1

```
Met Arg Ile Ala Val Ile Cys Phe Cys Leu Leu Gly Ile Thr Cys Ala
 1               5                  10                  15

Ile Pro Val Lys Gln Ala Asp Ser Gly Ser Ser Glu Glu Lys Gln Leu
                20                  25                  30

Tyr Asn Lys Tyr Pro Asp Ala Val Ala Thr Trp Leu Asn Pro Asp Pro
            35                  40                  45

Ser Gln Lys Gln Asn Leu Leu Ala Pro Gln Asn Ala Val Ser Ser Glu
        50                  55                  60

Glu Thr Asn Asp Phe Lys Gln Glu Thr Leu Pro Ser Lys Ser Asn Glu
65                  70                  75                  80

Ser His Asp His Met Asp Asp Met Asp Asp Glu Asp Asp Asp Asp His
                85                  90                  95
```

```
Val Asp Ser Gln Asp Ser Ile Asp Ser Asn Asp Ser Asp Asp Val Asp
            100                 105                 110

Asp Thr Asp Asp Ser His Gln Ser Asp Glu Ser His His Ser Asp Glu
        115                 120                 125

Ser Asp Glu Leu Val Thr Asp Phe Pro Thr Asp Leu Pro Ala Thr Glu
    130                 135                 140

Val Phe Thr Pro Val Val Pro Thr Val Asp Thr Tyr Asp Gly Arg Gly
145                 150                 155                 160

Asp Ser Val Val Tyr Gly Leu Arg Ser Lys Ser Lys Lys Phe Arg Arg
                165                 170                 175

Pro Asp Ile Gln Tyr Pro Asp Ala Thr Asp Glu Asp Ile Thr Ser His
            180                 185                 190

Met Glu Ser Glu Glu Leu Asn Gly Ala Tyr Lys Ala Ile Pro Val Ala
        195                 200                 205

Gln Asp Leu Asn Ala Pro Ser Asp Trp Asp Ser Arg Gly Lys Asp Ser
    210                 215                 220

Tyr Glu Thr Ser Gln Leu Asp Asp Gln Ser Ala Glu Thr His Ser His
225                 230                 235                 240

Lys Gln Ser Arg Leu Tyr Lys Arg Lys Ala Asn Asp Glu Ser Asn Glu
                245                 250                 255

His Ser Asp Val Ile Asp Ser Gln Glu Leu Ser Lys Val Ser Arg Glu
            260                 265                 270

Phe His Ser His Glu Phe His Ser His Glu Asp Met Leu Val Val Asp
        275                 280                 285

Pro Lys Ser Lys Glu Glu Asp Lys His Leu Lys Phe Arg Ile Ser His
    290                 295                 300

Glu Leu Asp Ser Ala Ser Ser Glu Val Asn
305                 310

<210> SEQ ID NO 2
<211> LENGTH: 6
<212> TYPE: PRT
<213> ORGANISM: Homo sapiens

<400> SEQUENCE: 2

Leu Val Leu Asp Pro Lys
  1               5

<210> SEQ ID NO 3
<211> LENGTH: 6
<212> TYPE: PRT
<213> ORGANISM: synthetic construct

<400> SEQUENCE: 3

Leu Val Val Asp Pro Lys
  1               5

<210> SEQ ID NO 4
<211> LENGTH: 5
<212> TYPE: PRT
<213> ORGANISM: Homo sapiens

<400> SEQUENCE: 4

Arg Gly Arg Asp Ser
  1               5

<210> SEQ ID NO 5
<211> LENGTH: 5
```

```
-continued

<212> TYPE: PRT
<213> ORGANISM: Homo sapiens

<400> SEQUENCE: 5

Gly Arg Gly Asp Ser
 1               5

<210> SEQ ID NO 6
<211> LENGTH: 32
<212> TYPE: PRT
<213> ORGANISM: Homo sapiens

<400> SEQUENCE: 6

Val Phe Thr Pro Val Val Pro Thr Val Asp Thr Tyr Asp Gly Arg Gly
 1               5                  10                  15

Asp Ser Val Val Tyr Gly Leu Arg Ser Lys Ser Lys Lys Phe Arg Arg
            20                  25                  30
```